United States Patent [19]

Shinzato

[11] Patent Number: 5,011,607
[45] Date of Patent: Apr. 30, 1991

[54] HEMODIAFILTRATION SYSTEM

[75] Inventor: Toru Shinzato, 104, Daido, Naha-shi, Okinawa-ken, Japan

[73] Assignees: Toru Shinzato, Okinawa; Medecs Co. Ltd., Aichi, both of Japan

[21] Appl. No.: 534,221

[22] Filed: Jun. 7, 1990

Related U.S. Application Data

[63] Continuation of Ser. No. 479,101, Mar. 25, 1983, which is a continuation of Ser. No. 267,451, May 27, 1981, abandoned.

[30] Foreign Application Priority Data

Feb. 24, 1979 [JP] Japan .................................. 54-21180

[51] Int. Cl.$^5$ ...................... B01D 61/24; B01D 61/28; B01D 61/32; B01D 63/02
[52] U.S. Cl. .................................... 210/637; 210/110; 210/134; 210/137; 210/321.65; 210/321.69; 210/321.8; 210/646; 210/741; 210/929
[58] Field of Search ............... 210/110, 117, 134, 136, 210/137, 139, 416.1, 637, 645, 646, 647, 741, 929, 321.65, 321.69, 321.79, 321.8

[56] References Cited

U.S. PATENT DOCUMENTS

| | | | |
|---|---|---|---|
| 3,570,672 | 3/1971 | Bach | 210/321.67 |
| 3,795,318 | 3/1974 | Crane et al. | 210/321.65 |
| 4,096,059 | 6/1978 | Pinkerton | 210/647 |
| 4,222,869 | 9/1980 | Kato | 210/646 |

Primary Examiner—W. Gary Jones
Attorney, Agent, or Firm—Browdy and Neimark

[57] ABSTRACT

A hemodiafiltration system which enables concurrent performance, in a single system, of hemodialysis and hemofiltration includes a dialyzer, consisting of a casing and at least one semipermeable membrane accommodated therein for dialyzing and purifying body fluid such as blood, plasma, etc., through contacting of the body fluid and dialyzate via the semipermeable membrane, and pumps for causing the dialyzate to flow through the dialyzer. A controller repeatedly changes the difference between the inflow amount of the dialyzate into the dialyzer per unit time and the outflow amount of the same from the dialyzer per unit time from a positive value to a negative value and then from negative to positive, whereby the repeated operation of taking or sucking out aqueous component or constituent and accompanying waste molecules from the body fluid followed by infusing or forcing a compensatory amount of dialyzate into the body fluid is made possible.

8 Claims, 2 Drawing Sheets

HEMODIAFILTRATION SYSTEM

CROSS-REFERENCE TO RELATED APPLICATIONS

The present application is a continuation of application Ser. No. 479,101 now abandoned, filed Mar. 25, 1983, which was a continuation of application Ser. No. 267,451, filed May 27, 1981, now abandoned.

BACKGROUND OF THE INVENTION

The present invention relates to a combined hemodialysis and hemofiltration (hemodiafiltration) process and apparatus and more particularly to a hemodiafiltration process and apparatus capable of causing dialyzate to migrate from a dialyzate side to a body fluid side of a membrane, and then causing an aqueous component or water to migrate from the body fluid side to the dialyzate side of the membrane in a dialyzer, repeatedly, for performing both dialysis and filtration to purify blood or other body fluid. The process and apparatus enable a highly efficient and easily executable purifying operation by means of making the process double purpose for hemofiltration (HF) and hemodialysis (HD). The present hemodiafiltration process and apparatus eliminate the replacement fluid introducing equipment which has been indispensable in conventional hemofiltration (HF) systems.

In recent years artificial kidneys, systems for purifying body fluid, such as blood or its ingredients, with the object of treating or maintaining the life of a patient suffering from renal insufficiency, have been widely employed. Such artificial kidneys include so-called dialyzers, which comprise semipermeable membranes, such as cuprammonium rayon membranes, in a casing, such membranes being of the film type, tube type, or hollow fiber type. The dialyzer of this type functions in the HD operation such that the body fluid, such as blood, is contacted with the dialyzate, the semipermeable membranes disposed therebetween for dialyzing and removing urea, uric acid, etc., accumulated in the body fluid of a patient (subject) so as to make the body fluid of almost normal solute concentration so as to be returned into the body of the patient. In the known HF operation, on the other hand, solution containing chiefly needless substances of middle and small molecular weight is removed from the blood by the filtering action of semipermeable membranes and solution containing indispensable substances is added to the blood to be returned to the body of the patient.

It is badly needed to have a system capable of executing both functions concurrently, so as to permit the removing capability of both HD and HF. No such a double purpose handy system capable of fulfilling both functions of HF and HD, in a single system, satisfactorily in high efficiency, has been developed yet. Another problem conventionally seen in the HF operation is the requirement for a replacement fluid introducing apparatus which infuses the replacement fluid containing the essential substances into the body and a regulating system for regulating at least one of the introducing speed of the replacement fluid and the filtering speed of the solution containing the needless substances from the side of the blood. Furthermore, the reducing amount and speed of the body fluid during the HF operation must be so controlled as to be agreeable with the predetermined schedule. A system attempting to satisfy such requirements inevitably becomes complicated in structure, highly precise, and consequently not simple in its operation mode. The disadvantages of the prior art are not confined to the above; other disadvantages include the necessity of the infusion fluid itself for the replacement of body fluid, and the problem of its transportation and storage. Due to all of the circumstances which have made the HF operation expensive and complex, development of a new hemodiafiltration system which is inexpensive in manufacturing cost and highly efficient in dialysis and filtration is badly needed.

SUMMARY OF THE INVENTION

The present invention was made from such a background. The primary object of this invention is therefore to provide a hemodiafiltration process and apparatus which enables concurrent performance, in a single system, of hemodialysis and hemofiltration.

Another object of this invention is to provide a hemodiafiltration process and apparatus capable of performing concurrent hemodialysis and hemofiltration operations of blood, exactly, safely and easily.

Still another object of this invention is to provide a hemodiafiltration system which is miniaturized, compact, simple and inexpensive, capable of nevertheless fulfilling blood purification by eliminating the conventional complex accessories such as the replacement fluid introducing equipment as well as the particular replacement fluid such as for intravenous drip infusion.

Other objects of this invention will become apparent to those skilled in the art from the following detailed description of the preferred embodiments when read in connection with the accompanying drawing.

For achieving those objects, a hemodiafiltration system in accordance with this invention is characteristically featured in providing a dialyzer consisting of a casing and at least one semipermeable membrane accommodated therein for purifying body fluid such as blood, plasma, etc., through hemodialysis by contacting of the body fluid and dialyzate via the semipermeable membrane, and flowing means for flowing the dialyzate through the dialyzer. The system further includes a flowing amount varying means for repeatedly changing the difference between the inflow amount of the dialyzate into the dialyzer per unit time and the outflow amount of the same from the dialyzer per unit time from a positive value to a negative value and also from negative to positive, whereby the repeated operation of infusing or forcing dialyzate into the body fluid and subsequently taking or sucking out aqueous component or constituent from the body fluid is made possible. In the course of the transition or migration of aqueous component from the body fluid side to the dialyzate side, there occurs the migration of solute (waste substances) constituted of middle and small molecules (hemofiltration), which means the larger the amount of extracted aqueous component removed, the larger the amount of waste substances removed. On the other hand, any shortage of aqueous component in the body fluid can be compensated by means of making positive the difference of the inflow amount of the dialyzate into the dialyzer per unit time minus the outflow amount of the dialyzate from the dialyzer per unit time; that is to say, the dialyzate containing essential substances is automatically forced to migrate to the body fluid side as the replacement fluid, through the semipermeable membrane, for the corresponding amount of aqueous component which has been extracted or sucked out of the body fluid. Thus, the single system can concurrently perform the traditionally so-called HF operation and the HD operation.

The hemodiafiltration system herewith referred to is easily operable and able to eliminate the necessity of a particularly prepared infusion fluid for replacement of body fluid and special equipment for introducing the same. By this invention the hemodiafiltration system has been made compact, simple, and remarkably inexpensive through eliminating troublesome operations.

DETAILED DESCRIPTION OF THE PREFERRED EMBODIMENTS

Figure 1:
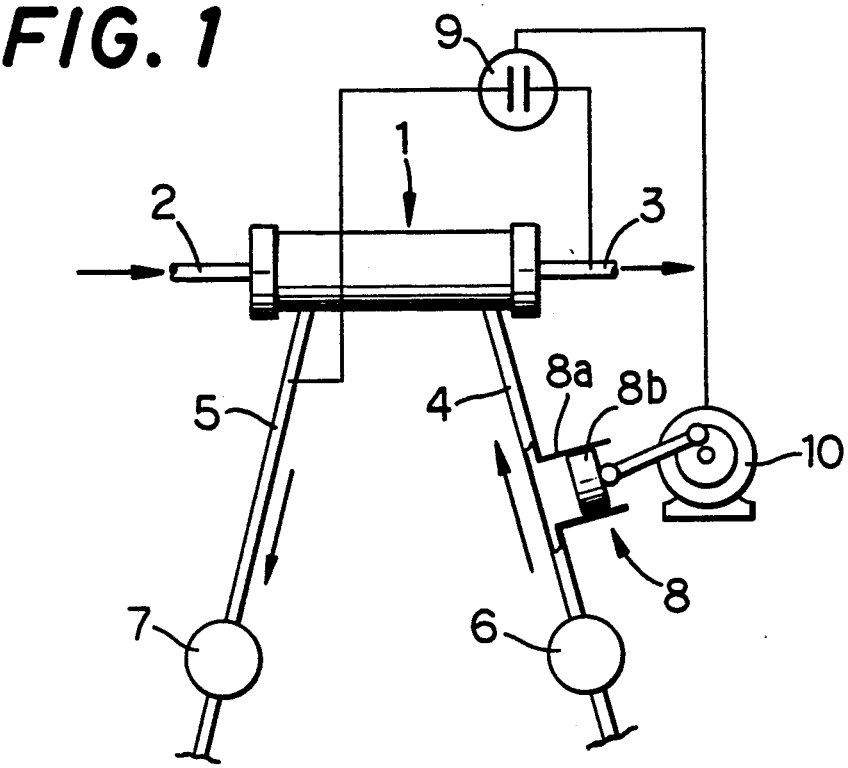
FIG. 1 is a schematic diagram showing an embodiment of a hemodiafiltration system in accordance with the present invention.

The present invention will be described referring to the illustrated embodiments in the drawings, in which FIG. 1 concretely shows a system thereof. Numeral 1 designates generally a known dialyzer as a blood purifying device consisting of a casing and at least one semipermeable membrane accommodated therein. The semipermeable membrane is of hollow fiber type, which may alternatively be of film type or tube type. The dialyzer 1 is provided with a blood supply passage 2 connected thereto for introducing blood from the body of a patient or subject and a blood discharge passage 3 similarly connected thereto for returning the purified blood in the dialyzer 1 back to the body of the patient.

The dialyzer 1 is further provided with a dialyzate supply passage 4 for introducing the dialyzate thereinto and a dialyzate discharge passage 5 for discharging the dialyzate which has contacted the blood in the dialyzer 1 via the semipermeable membrane so as to absorb or take out unnecessary or harmful substances from the blood due to the dialyzing and filtering action of the semipermeable membrane.

Figure 3:
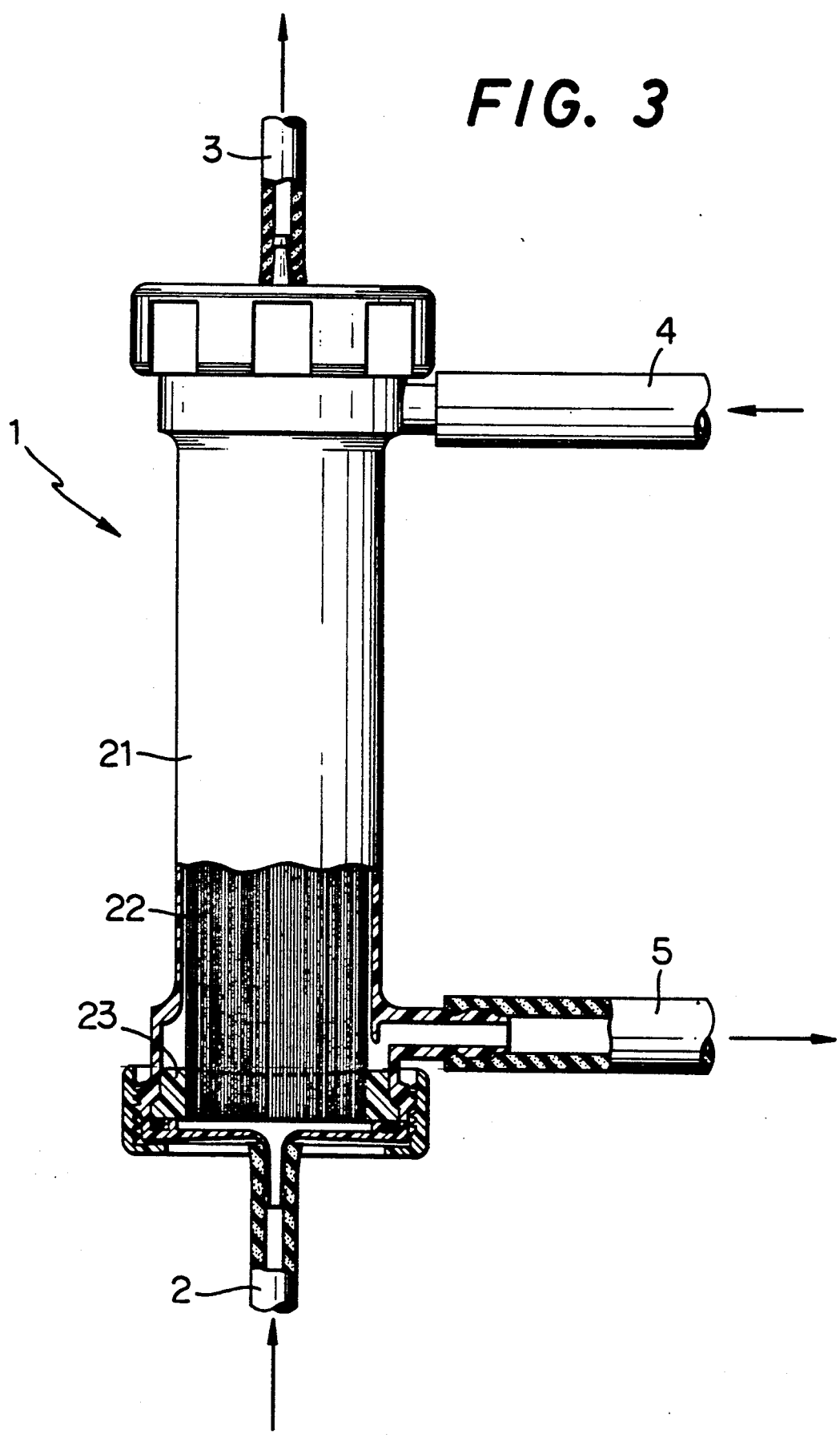
FIG. 3 is a schematic axial sectional view, partly shown, of an example of a dialyzer employed in the present invention.

The internal structure of the dialyzer 1 is known to those skilled in the art, and an example of such is shown in FIG. 3. In a casing 21 thousands of hollow fibers 22, being semipermeable membranes made of a synthetic or natural polymer of polymethylmethacrylate, polyacrylonitrile, cuprammonium rayon, etc., are accommodated, and the blood supplied through the blood supply passage 2 is passed through the hollow spaces of the hollow fibers 22 from one end thereof and is then discharged into the blood discharge passage 3. The dialyzate introduced through the dialyzate supply passage 4 is, upon having passed through gaps between the hollow fibers, discharged through the dialyzate discharge passage 5. Numeral 23 designates a seal.

In the dialyzate supply passage 4 and the dialyzate discharge passage 5, there are provided respectively a dialyzate supply pump 6, with a predetermined discharge capacity and acting as a dialyzate supplying mechanism, and a dialyzate discharge pump 7, with a larger discharge capacity than the former pumps by the predetermined amount of the aqueous component or water being removed from the patient's body. In the dialyzate supply passage 4, a volume changing device 8, capable of varying the inner volume capacity thereof by its cylinder 8a and a piston 8b, is mounted between the dialyzate supply pump 6 and the dialyzer 1. This embodiment of a hemodiafiltration system is further provided with a controlling device 9 for controlling a driving mechanism 10 of the volume changing device 8 such that the difference of pressure detected in the blood discharge passage 3 and the dialyzate discharge passage 5 by a respective pressure transducer may be adjusted respectively to be a predetermined value in response to the timing of the inner capacity decreasing and increasing of the volume changing device 8.

When blood purification is performed in a system of such structure, the operation must be executed such that the difference of the discharge amount in the dialyzate discharge pump 7 and the dialyzate supply pump 6 is made equal to the expected difference of the amount of fluid supplied to the patient's body minus the extracted or filtered amount from the body. Thus, the dialyzate in the dialyzer 1 is kept at a constant flow with a predetermined flow amount, while the inner capacity or volume of the volume changing device 8 is timewise varied, i.e., increased and decreased according to the lapse of time, gradually, for example, from 0 ml to 40 ml over a first time span and from 40 ml to 0 ml again over a second time span subsequent to the first time span. This causes an increase and decrease of the inner capacity of the whole passage from the dialyzate supply pump 6 through the dialyzer 1 to the dialyzate discharge pump 7.

Decreasing of the inner capacity of the volume changing device 8 makes the dialyzate positive in pressure, with the result of forcing the dialyzate to migrate into the blood through the semipermeable membranes in the dialyzer 1 during the second time span. Increasing of the inner capacity of the volume changing device 8 makes, on the contrary, the dialyzate negative in pressure, with a result of effecting hemofiltration of the aqueous component of the blood out into the dialyzate during the first time span. Alternate increasing and decreasing of the inner capacity during an entire period of hemodialysis of the blood, balances the amount of aqueous component filtered from the blood and the amount of dialyzate migrated into the blood. In other words, the shortage amount of the aqueous component caused by the migration of aqueous component from the blood side to the dialyzate side due to the capacity increase in the volume changing device 8 is compensated for by the dialyzate migration into the blood due to the capacity decrease in the volume changing device 8, thereby completely eliminating the need for specially prepared infusion fluid for the replacement of body fluid and the equipment for introducing such fluid. Additionally, the difference of pressure in the blood discharge passage 3 and the dialyzate discharge passage 5 is so controlled as to be equal to a respectively predetermined value in response to the increase and decrease of the inner capacity of the volume changing device 8 by the control of the driving mechanism 10 through the action of the control device 9. By such a mechanism, the semipermeable membranes are ensured of safely performing the maximum filtering capability thereof.

The above described system performs, while carrying out on one hand hemodialysis (HD) continually, the replacement of the body fluid effectively, safely, and exactly, and does not need the traditional complicated devices for regulating the filtered amount and the infused amount of the replacement fluid nor the particular infusion fluid for replacement of body fluid. It has made possible not only rendering the whole system simple, compact, and inexpensive but also rendering the hemodiafiltration (HDF) method itself safe and inexpensive.

Figure 2:
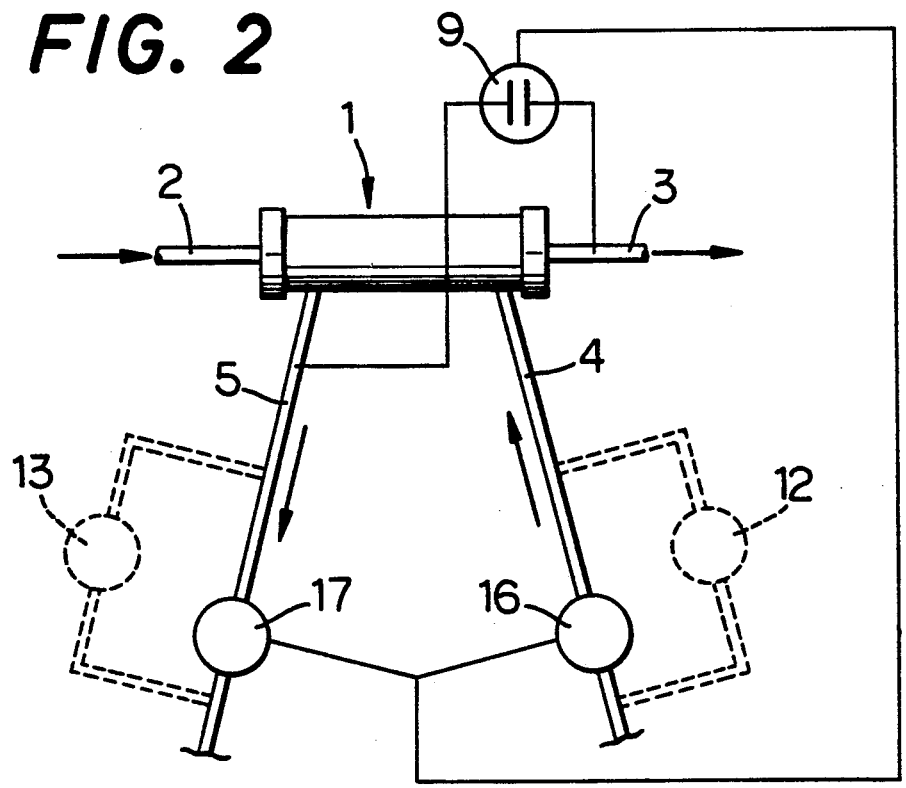
FIG. 2 is a schematic diagram showing another embodiment of a hemodiafiltration system in accordance with the present invention.

Another embodiment of this invention will be described with reference to FIG. 2, in which identical numerals as in FIG. 1 designate identical or like parts. In this embodiment, there is no volume changing device 8 as in the previous one; instead, the discharge amount or capacity of the dialyzate supply pump 16 and/or the dialyzate discharge pump 17 is made variable, which distinguishes the present embodiment from the previous one.

Assume an example wherein the discharge amount of the dialyzate supply pump 16 is constant while that of the dialyzate discharge pump 17 is variable; in a case wherein the discharge amount of the latter is larger than that of the former the dialyzate is under the influence of negative pressure, causing hemofiltration, i.e., migration in the dialyzer 1 of the aqueous component of the blood into the dialyzate over a first time span. If the discharge amount of the latter pump is smaller than that of the former, the dialyzate is placed under the influence of positive pressure, with a result of migration of the dialyzate into the blood over a second time span subsequent to the first time span.

Assume again another example wherein the discharge amount of the dialyzate supply pump 16 is variable, while that of the dialyzate discharge pump 17 is kept constant; in a case wherein the discharge amount of the former is larger than that of the latter, the dialyzate is placed under the influence of positive pressure, and in the inverted case the dialyzate is placed under the influence of negative pressure, causing in either case migration of the aqueous component between the blood and the dialyzate. If both pumps (16, 17) are pressure variable, the difference of the discharge amount between the two determines the positive and negative relation of the pressure coming on the dialyzate. Alternate increase and decrease of the discharge amount of the variable pumps (16, 17) causes, respectively, migration of the dialyzate into the blood and filtration of the aqueous component from the blood. Repetition of this type of operation makes the dialysis of the body fluid, while performing filtration and replacement thereof, possible just like in the previous embodiment.

The above description relates to the first and second embodiments, but this invention is by no means limited to those. The disclosure and statement of the embodiments does not limit the invention itself at all. Various modifications and alterations are possible for those skilled in the art within the spirit and scope of this invention. For example, the volume changing device disposed as a means for varying the inner capacity of the dialyzate flowing passage may be substituted by a bag- or sack-like device capable of varying the inner capacity thereof by applying pressure or drawing a volume. The method of varying the dialyzate migration amount and the aqueous component filter amount to and from the dialyzer by means of the dialyzate supply pump and the dialyzate discharge pump may be modified such that a third pump 12 and a fourth pump 13, shown with a broken line in FIG. 2, disposed respectively by-passing the above-mentioned two pumps, are alternately operated, while the earlier mentioned two pumps are fixed at a predetermined value in respect of the discharge amount, for achieving the same object.

The volume changing device 8, which is disposed in the dialyzate supply passage 4 in the first embodiment, may be placed anywhere in the flowing passage ranging from the dialyzate supply pump 6 through the dialyzer 1 to the dialyzate discharge pump 7.

From the above description the present invention can be summarized as having achieved the object of performing the replacement of the body fluid, the dialysis, etc., under an exact, safe and easy control, without employing the traditional inevitable complex accessories such as the replacement fluid introducing equipment and particular replacement fluid such as for intravenous drip infusion. It has characteristically attained the object of making blood purification in a simple, compact, and inexpensive system possible.

What is claimed is:

1. A process for purifying a body fluid by combined dialysis and filtration, comprising:
    (a) flowing the body fluid to be purified past one side of a semi-permeable membrane;
    (b) simultaneously flowing dialyzate past the opposite side of said semi-permeable membrane, said flowing steps (a) and (b) being under conditions sufficient to permit purification of the body fluid by dialysis;
    (c) over a first time span, and concurrently with said dialysis, causing the pressure on the dialyzate side of said semi-permeable membrane to be less than the pressure on the body fluid side thereof, said first time span and said pressure difference being sufficient to force middle and small molecular weight molecules to travel from the body fluid side to the dialyzate side of said semi-permeable membrane by filtration;
    (d) over a second time span, subsequent to said first time span and concurrently with said dialysis, causing the pressure on the dialyzate side of said semi-permeable membrane to be greater than the pressure on the body fluid side thereof, said second time span and said pressure difference being sufficient to cause infusion through said semi-permeable membrane of an amount of dialyzate which is compensatory for the amount of fluid passing from the body fluid side to the dialyzate side during said first time span; and
    (e) repeating said steps (c) and (d) in a manner such that alternating pressure differences occur across the same portion of said semi-permeable membrane at a rate which ensures efficient combined filtration and dialysis.

2. A process in accordance with claim 1, wherein said steps (c) and (d) are accomplished by means of a pair of pumps in the stream of flowing dialyzate, one pump being upstream of said semi-permeable membrane and the other pump being downstream thereof, at least one of said pumps being a variable pump, said pumps being connected to a control means for varying the discharge amount of said at least one variable pump in order to cause the pressure differences recited in steps (c) and (d).

3. A process in accordance with claim 1, wherein said steps (c) and (d) are accomplished by means of a dialyzate flow passage having a variable volume capacity, and a control means for increasing and decreasing the volume capacity of the dialyzate flow passage in order to cause the pressure differences recited in steps (c) and (d).

4. A process in accordance with claim 1, wherein said body fluid is blood, said dialysis is hemodialysis and said filtration is hemofiltration.

5. An apparatus for purifying a body fluid by combined dialysis and filtration, comprising
 (a) dialyzer means including a casing, a semi-permeable membrane, dialyzate inlet and outlet passages, and body fluid inlet and outlet passages, for permitting the simultaneous flow of dialyzate on one side of the membrane and flow of body fluid on the other side of the membrane;
 (b) pressure differential means communicating with said dialyzer means for causing variation of the pressure on the dialyzate side of said semi-permeable membrane with respect to that on the body fluid side thereof such that said pressure can be varied between a state at which the pressure on the dialyzate side of said semi-permeable membrane is less than the pressure on the body fluid side thereof and a state at which the pressure on the dialyzate side of said semi-permeable membrane is greater than the pressure on the body fluid side thereof; and
 (c) control means connected to said pressure differential means for controlling said pressure differential means, when the apparatus is in use, to cause the pressure on the dialyzate side of said semi-permeable membrane to be less than the pressure on the body fluid side thereof for sufficient time and with a sufficient pressure difference to force middle and small molecular weight molecules to travel from the body fluid side to the dialyzate side of said semi-permeable membrane by filtration, to subsequently cause the pressure on the dialyzate side of said semi-permeable membrane to be greater than the pressure on the body fluid side thereof for a period of time and with sufficient pressure difference to cause infusion through said semi-permeable membrane of an amount of dialyzate which is compensatory for the amount of fluid passing from the body fluid side to the dialyzate side during said first time span and for repeating said first and second time spans in a manner such that alternating pressure differences occur across the same portion of said semi-permeable membrane at a rate which ensures sufficient combined filtration and dialysis.

6. An apparatus in accordance with claim 5, wherein said control means include measuring means for measuring the pressure in said body fluid discharge passage and said dialyzate discharge passage and for using the information obtained therefrom in controlling said pressure differential means.

7. An apparatus in accordance with claim 5, wherein said pressure differential means includes first pumping means communicating with said dialyzate inlet passage for pumping dialyzate into said dialyzer means, second pumping means communicating with said dialyzate outlet passage for pumping dialyzate out of said dialyzer means, said first pump having a first predetermined discharge capacity and said second pump having a second predetermined discharge capacity larger than that of said first pump, and volume varying means for permitting the variation of the internal volume of the dialyzate passage between said first and second pumping means, and wherein said control means controls the operation of said volume differential means.

8. An apparatus in accordance with claim 5, wherein said pressure differential means includes first pumping means communicating with said dialyzate inlet passage for pumping dialyzate into said dialyzer means and second pumping means communicating with said dialyzate outlet passage for pumping dialyzate out of said dialyzer means, wherein at least one of said first and second pumping means are variable in discharge capacity and wherein said control means controls the variation of discharge capacity of said at least one variable capacity pumping means.

* * * * *